United States Patent [19]

Jinno et al.

[11] 4,164,413

[45] Aug. 14, 1979

[54] METHOD FOR PROMOTING GROWTH OF PLANTS WITH CATIONIC POLYMERS

[75] Inventors: Naoyoshi Jinno, Ibaraki; Takeo Satomi, Nishinomiya; Shigenao Kawakami, Hirakata; Tatsumi Shibata, Toyonaka; Shin-ichi Isaoka, Minoo, all of Japan

[73] Assignee: Sumitomo Chemical Company, Ltd., Osaka, Japan

[21] Appl. No.: 902,692

[22] Filed: May 4, 1978

[30] Foreign Application Priority Data

May 23, 1977 [JP] Japan ................... 52-60269

[51] Int. Cl.$^2$ .......................... A01N 5/00; C05F 7/00
[52] U.S. Cl. ............................ 71/103; 71/77; 71/105; 71/106; 71/118; 71/13; 71/27
[58] Field of Search ............... 71/106, 118, 105, 103, 71/77, 27, 13

[56] References Cited

U.S. PATENT DOCUMENTS 2,745,815 5/1956 Mussell .................... 71/27 X

FOREIGN PATENT DOCUMENTS 4810535 4/1969 Japan.

Primary Examiner—Catherine L. Mills
Attorney, Agent, or Firm—Birch, Stewart, Kolasch & Birch

[57] ABSTRACT

The growth of plants is promoted using a water-soluble cationic polymer obtained by polymerization of a quarternary ammonium compound of the following formula (I) alone or together with other vinyl monomers,

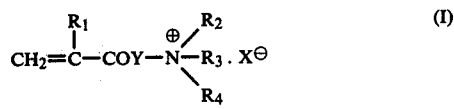

wherein $R_1$ is hydrogen or methyl, $R_2$ and $R_3$ are each a lower alkyl, $R_4$ is a lower alkyl, allyl, a hydroxy(-lower)-alkyl, benzyl or —CH$_2$COO(CH$_2$)$_m$CH$_3$ group (in which m is 0 or 1), X is a halogen or methylsulfate and Y is —O(CH$_2$)$_n$—, —NH—(CH$_2$)$_n$— (in which n is 1 to 4) or

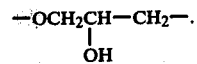

9 Claims, No Drawings

METHOD FOR PROMOTING GROWTH OF PLANTS WITH CATIONIC POLYMERS

The present invention relates to a method for promoting growth of plants with water-soluble cationic polymers.

There is well known a method of promoting growth of plants by adding water-soluble high polymers alone or together with other natural or chemical fertilizers to soil and, thereby conditioning the physical structure of the soil so as to meet the growth of plants. According to this method, fine soil particles frequently present in infertile lands are flocculated into large particles by means of a flocculating action of the water-soluble high polymers, by which the passage of air in soil, water retention, drainage and fertilizer retention of soil are improved and, as the result, the growth of plants in soil is promoted. Besides, this flocculation of soil particles effect prevention of soil from erosion by rain and the like.

As the water-soluble high polymers applicable to this known method, there may be exemplified homopolymers of monomers such as acrylamide, acrylic acid, dimethylaminoethyl methacrylate, vinylpyridine, and vinylsulfonic acid, copolymers of said monomers with other copolymerizable monomers, and copolymers of said monomers with unsaturated dibasic acids such as maleic acid and fumaric acid. In some cases, however, these high polymers have to be limited in their use because of their growth inhibiting effects against plants.

The inventors have extensively studied the plant growth promoting effect of many kinds of high polymer and have found that some specified water-soluble cationic polymers are effective for promoting the germination and growth of plants even in water.

An object of the present invention is to provide an improved method for promoting germination and growth of plants using specific water-soluble cationic polymers. Another object of the invention is to provide a flocculating agent having no inhibitory effect on the germination and growth of plants. These and other objects of the invention will be apparent from the following description.

The present method of promoting growth of plants is characterized by using a water-soluble cationic polymer which is produced by polymerization of a quaternary ammonium compound of the following formula (I) alone or together with one or more other vinyl monomers,

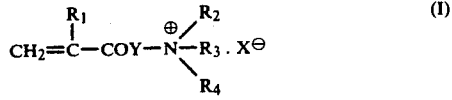
(I)

wherein $R_1$ is hydrogen or methyl, $R_2$ and $R_3$ are each a lower alkyl, $R_4$ is a lower alkyl, allyl, a hydroxy(lower)-alkyl, benzyl or $-CH_2COO(CH_2)_mCH_3$ group (in which m is 0 or 1), X is a halogen or methylsulfate and Y is $-O(CH_2)_n-$, $-NH-(CH_2)_n-$ (in which n is 1 to 4) or

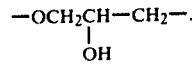

In the present specification, "lower alkyl" denotes an alkyl having 1 to 4 carbon atoms, such as methyl, ethyl, propyl, isopropyl, butyl, isobutyl, or tert-butyl. "Hydroxy-(lower)alkyl" denotes hydroxyalkyl having 1 to 3 carbon atoms in the alkyl moiety, such as hydroxymethyl, hydroxyethyl, or hydroxypropyl. "Halogen" denotes fluorine, chlorine, bromine or iodine.

The water-soluble cationic polymers of the present invention have an excellent plant growth promoting effect when applied to soil as a flocculating agent. When observed on the germination and growth of plants in water containing the water-soluble cationic polymers of the present invention, the polymers showed a remarkable growth promoting effect, too. Moreover, in the dehydration treatment of organic sludge with a flocculating agent, the treated water contaminated with a trace amount of the agent occasionally flows into paddy fields and may show an inhibitory effect on growth of plants. However, when the specified cationic polymers of the present invention are used as a flocculating agent, such an inhibitory effect is not observed, but the growth of plants is rather favorably promoted.

The quaternary ammonium compounds of the formula (I) used in the present invention include water-soluble monomers prepared by quaternarizing a dialkylaminoalkyl (methy)acrylate (e.g. dimethylaminoethyl (meth)acrylate, diethylaminoethyl (meth)acrylate, or diethylaminohydroxypropyl acrylate) or an N-dialkylaminoalkyl-acrylamide (e.g. N-dimethylamino-n-propyl-acrylamide, or N-dimethylaminoethylacrylamide) with a quaternarizing agent (e.g. methyl chloride, ethyl chloride, methyl bromide, ethyl bromide, methyl iodide, ethyl iodide, benzyl chloride or dimethyl sulfate). Particularly, a superior plant growth promoting effect is obtained when a quaternary ammonium compound produced by quaternarizing dimethylaminoethyl methacrylate with methyl chloride or dimethyl sulfate is used.

The other vinyl monomers copolymerizable with the aforesaid compound (I) include water-soluble monomers such as acrylamide and (meth)acrylic acid. Copolymers with a hydrophobic compound such as methyl (meth)acrylate, styrene or acrylonitrile may also be used, but the degree of copolymerization should be within such a range that the produced high polymers do not lose solubility in water.

The desired water-soluble cationic polymer may be prepared by homopolymerizing the quaternary ammonium compound of the formula (I) or copolymerizing the quaternary ammonium compound of the formula (I) and one or more other vinyl monomers as mentioned above by conventional polymerization methods such as solution polymerization, emulsion polymerization and precipitation polymerization. The polymerization may be carried out under the conditions of a polymerization temperature: under the reflux temperature of the reaction solvents, a polymerization period of time: 2-24 hours. The polymer has an intrinsic viscosity (at 30° C. in 1N-NaNO₃) of larger than 0.1.

The present cationic polymer can be applied as it is or in the form of an aqueous solution either to soil or to water wherein plants are grown or to be grown. When the cationic polymers are applied to soil, they are used in an amount of 0.01 to 1.0% by weight based on the weight of soil. When they are added to water, it is preferably to use in an amount of 0.01 to 0.5% by weight based on the weight of water. When the amounts are below these ranges, the growth promoting effect can not be expected.

Recently, activated sludge treatments of nightsoil and waste water from living have been widely carried out, and the surplus sludge from this treatment containing a large amount of organic substances can be dehydrated with a dehydrating agent. The dehydrated sludge thus obtained is usually disposed by burning off or by employing for reclamation. In case of burning, however, a great expense is required for fuels and in addition injurious gases an undesirably generate. Besides, in case of reclamation, injurious gases such as methane gas are also generate. On the contrary to these conventional dehydrating agents, the specified water-soluble cationic polymers of the present invention can be used as the dehydrating agent or flocculating agent for dehydrating surplus sludge in the activated sludge treatment without such defects, and furthermore, the resulting dehydrated sludge cake containing the polymers also displays a very superior plant growth promoting effect.

Thus, the present invention provides also a method for promoting growth of plants by applying the cationic polymers to a surplus sludge produced in an activated sludge treatment and then applying the resulting dehydrated sludge to soil. According to this method, while the sludge cake obtained by using the conventional dehydrating agents is hardly dealt with, the sludge cake obtained by using the present cationic polymers can not only be effectively and safely disposed of by putting back the cake to farm, but can also be used for promoting the growth of plants. The sludge cake containing the present cationic polymers can preferably be applied to soil in an amount of up to about 1.0% by weight, preferably from 0.01 to 0.5% by weight, (converted to the cationic polymer) based on the weight of soil.

The plants, to which the cationic polymers of the present invention are applicable for promoting the growth, are not specifically limited, but they are particularly effective for vereals (e.g. rice plant, wheat and barnyard grass), fruit-eatable vegetables (e.g. cucumber and tomato), radish, carrot, rape, or the like. Moreover, the growth promoting effect of the cationic polymers is exerted on any portion of the plants, such as roots, leaves and stems.

The present invention will be illustrated with reference to the following examples, but is not limited thereto.

EXAMPLE 1

Each of the polymers shown in Table 1 was uniformly mixed with soil in an amount of 0.1% by weight based on the soil and filled in a pot of about 10 cm in diameter. Three to eight seeds of each of rice plant, radish, rape and tomato were showed in separate pots and grown up at 20° to 25° C. for 20 days in a greenhouse. The weight of stem and root of each plant was measured after washing off the soil from the pot, washing the plant well, and removing water sufficiently. The results are shown in Table 1. The values were expressed in a percentage to the values of control.

The symbols, A to L, in Table 1 mean the following monomers:

A: $\beta$-Methacryloxyethyl trimethylammonium chloride
B: $\beta$-Acryloxyethyl trimethylammonium chloride
C: $\beta$-Methacryloxyhydroxypropyl trimethylammonium chloride
D: N-($\beta$-Trimethylammonium chloride)ethylmethacrylamide
E: $\beta$-Methacryloxyethyl trimethylammonium methylsulfate
F: Acrylamide
G: Acrylonitrile
H: Acrylic acid
I: Methyl methacrylate
J: Maleic acid
K: Styrene
L: Dimethylaminoethyl methacrylate (These symbols are used likewise in the following examples).

Table 1

|  | Polymer Control | Weight of stem | | | | Weight of root | | | |
|---|---|---|---|---|---|---|---|---|---|
|  |  | Rice plant 100 | Radish 100 | Rape 100 | Tomato 100 | Rice plant 100 | Radish 100 | Rape 100 | Tomato 100 |
| Present example | Polymer of A | 133 | 138 | 147 | 129 | 129 | 131 | 145 | 121 |
|  | Polymer of B | 119 | 126 | 123 | 121 | 112 | 121 | 128 | 126 |
|  | Polymer of C | 125 | 121 | 116 | 118 | 123 | 118 | 123 | 121 |
|  | Polymer of D | 115 | 123 | 110 | 127 | 121 | 135 | 120 | 127 |
|  | Polymer of E | 130 | 136 | 138 | 135 | 121 | 141 | 143 | 140 |
|  | Copolymer( A : F = 1 : 1) | 151 | 168 | 175 | 158 | 137 | 141 | 164 | 132 |
|  | Copolymer (C : F = 1 : 1) | 129 | 139 | 135 | 141 | 131 | 127 | 138 | 129 |
|  | Copolymer (E : F = 1 : 1) | 147 | 148 | 139 | 155 | 121 | 129 | 135 | 123 |
|  | Terpolymer (A : F : G = 4.5 : 4.5 : 1) | 117 | 123 | 116 | 112 | 120 | 119 | 124 | 118 |
|  | Terpolymer (A : F : I = 4.5 : 4.5 : 1) | 122 | 116 | 115 | 118 | 115 | 109 | 119 | 116 |
| Reference example | Polymer of F | 109 | 106 | 101 | 112 | 103 | 105 | 100 | 105 |
|  | Polymer of H | 102 | 107 | 108 | 107 | 105 | 101 | 107 | 109 |
|  | Copolymer (F : H = 7 : 3) | 109 | 106 | 112 | 102 | 103 | 105 | 106 | 105 |
|  | Polymer of L | 114 | 118 | 113 | 109 | 105 | 112 | 109 | 113 |
|  | Copolymer (J : K = 1 : 1) | 107 | 105 | 98 | 102 | 101 | 103 | 101 | 106 |

EXAMPLE 2

Using the copolymers comprising monomer components, A and F, in varying weight ratios, the plant growth promoting effect was measured in the same manner as in Example 1. The results are shown in Table 2.

Table 2

| Polymer A : F Weight ratio Control | Weight of stem | | | Weight of root | | |
|---|---|---|---|---|---|---|
|  | Rice plant 100 | Radish 100 | Rape 100 | Rice plant 100 | Radish 100 | Rape 100 |
| 100 : 0 | 133 | 138 | 147 | 129 | 131 | 145 |
| 80 : 20 | 147 | 149 | 151 | 132 | 138 | 137 |
| 50 : 50 | 151 | 168 | 175 | 137 | 141 | 164 |
| 30 : 70 | 155 | 151 | 171 | 147 | 145 | 163 |

Table 2-continued

| Polymer A : F Weight ratio | Weight of stem | | | Weight of root | | |
|---|---|---|---|---|---|---|
| | Rice plant | Radish | Rape | Rice plant | Radish | Rape |
| Control | 100 | 100 | 100 | 100 | 100 | 100 |
| 10 : 90 | 147 | 153 | 151 | 140 | 139 | 154 |
| 0 : 100 | 109 | 106 | 101 | 103 | 105 | 100 |

EXAMPLE 3

Using various amounts of polymers, the growth of plants was observed in the same manner as in Example 1. The results are shown in Table 3.

Table 3

| Polymer | Dosage to soil (% by weight) | Weight of stem | | | Weight of root | | |
|---|---|---|---|---|---|---|---|
| | | Rice plant | Rad-ish | Rape | Rice plant | Rad-ish | Rape |
| Control | — | 100 | 100 | 100 | 100 | 100 | 100 |
| Copolymer (A : F = 50 : 50) | 0.5 | 118 | 134 | 126 | 103 | 103 | 109 |
| | 0.1 | 151 | 168 | 175 | 137 | 141 | 164 |
| | 0.01 | 146 | 158 | 163 | 144 | 147 | 138 |
| | 0.003 | 121 | 107 | 101 | 103 | 98 | 100 |
| Copolymer (A : F = 30 : 70) | 0.5 | 127 | 125 | 105 | 135 | 101 | 147 |
| | 0.1 | 155 | 151 | 171 | 147 | 145 | 163 |
| | 0.01 | 109 | 112 | 118 | 123 | 115 | 137 |
| | 0.003 | 98 | 103 | 105 | 101 | 107 | 101 |
| Polymer of A | 0.1 | 133 | 138 | 147 | 129 | 131 | 145 |
| | 0.01 | 141 | 151 | 145 | 128 | 127 | 136 |
| Polymer of E | 0.1 | 130 | 136 | 138 | 121 | 141 | 143 |
| | 0.01 | 116 | 132 | 123 | 112 | 133 | 127 |

EXAMPLE 4

Aqueous solutions (each 5 cc) of the test polymer having a pre-determined concentration were separately placed in a Petri dish (diameter: 10 cm). The seeds of rice plant, barnyard grass and cucumber were each sowed in separate Petri dishes and grown up for 5 to 6 hours in an artificial lighting room at about 25° C. The weight of bud and root of each plant was measured, and the values obtained were averaged at every test plot and expressed in a percentage to control. The results are shown in Table 4.

Table 4

| | Polymer | Concentration (weight %) | Rice plant | | Barnyard grass | | Cucumber | |
|---|---|---|---|---|---|---|---|---|
| | | | Bud | Root | Bud | Root | Bud | Root |
| Control | | — | 100 | 100 | 100 | 100 | 100 | 100 |
| Present example | Copolymer (A : F = 30 : 70) | 0.3 | 105 | 150 | 125 | 80 | 145 | 100 |
| | | 0.1 | 120 | 155 | 120 | 115 | 130 | 100 |
| | | 0.01 | 110 | 120 | 110 | 115 | 115 | 105 |
| Reference example | Copolymer (H : F = 30 : 70) | 0.3 | 30 | 50 | 60 | 70 | 30 | 40 |
| | | 0.1 | 90 | 90 | 80 | 90 | 50 | 70 |
| | | 0.01 | 100 | 100 | 95 | 90 | 100 | 90 |

EXAMPLE 5

Excess sludge resulting from the activated sludge treatment of nightsoil was flocculated by adding a pre-determined amount of cationic polymer as a flocculating agent, and dehydrated by a small centrifugal dehydrator (800 rpm × 5 minutes). The resulting sludge cake was added to soil (dry weight: 5.6 kg) in a pot of 25 cm × 35 cm × 10 cm (height) so as to obtain a pre-determined ratio of dry weight to solid content of sludge cake. The both were then uniformly mixed.

Seeds of wheat were sowed in the pot, and after 2 months the plant height and top weight (fresh weight above the ground) were measured. The results are shown in Table 5.

The flocculating agents used in this example were as follows:
Flocculating agent 1: Copolymer (A:F=1:1)
Flocculating agent 2: Copolymer (A:F=1:9)
Flocculating agent 3: Polymer of A
Comparative flocculating agent: Mannich type cationic polymer The term "None" in the column of flocculating agent means the case wherein the surplus sludge was filtered under reduced pressure with no addition of flocculating agent and the sludge cake thus obtained was used for test. The water content of each sludge cake was adjusted to about 80%.

Table 5

| Flocculating agent | Solid content/ dry weight (%) | Cationic polymer/ dry weight (%) | Plant height | Top weight |
|---|---|---|---|---|
| None | 3 | — | 109 | 115 |
| Flocculating agent 1 | 3 | 0.3 | 133 | 151 |
| Flocculating agent 1 | 3 | 0.05 | 131 | 148 |
| Flocculating agent 2 | 3 | 0.05 | 137 | 155 |
| Flocculating agent 3 | 3 | 0.05 | 119 | 129 |
| Comparative flocculating agent | 3 | 0.05 | 106 | 109 |
| None | 15 | — | 121 | 129 |
| Flocculating agent 1 | 15 | 0.75 | 131 | 165 |
| Flocculating agent 1 | 15 | 0.25 | 138 | 153 |
| Flocculating agent 2 | 15 | 0.25 | 135 | 171 |
| Flocculating agent 3 | 15 | 0.25 | 127 | 146 |
| Comparative flocculating agent | 15 | 0.25 | 118 | 125 |

All the numerical values are expressed in ratio to the case wherein no sludge cake was added, with the case as 100.

What is claimed is:

1. A method for promoting the growth of plants comprising contacting the plants with an effective amount of a water-soluble cationic polymer obtained by polymerization of a quarternary ammonium compound of the formula (I) alone or together with at least one of other vinyl monomers, the formula (I) being

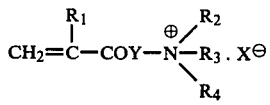  (I)

wherein $R_1$ is hydrogen or methyl, $R_2$ and $R_3$ are each an alkyl having 1 to 4 carbon atoms, $R_4$ is an alkyl having 1 to 4 carbon atoms, allyl, a hydroxyalkyl having 1 to 3 carbon atoms, benzyl or $-CH_2COO(CH_2)_mCH_3$ group (in which m is 0 or 1), x is a halogen or methylsulfate and Y is $-O(CH_2)_n-$, $-NH-(CH_2)_n-$ (in which n is 1 to 4) or

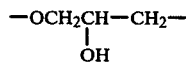

the other vinyl monomers being water soluble or hydrophobic, and the degree of copolymerization being within such a range that the produced cationic polymer does not lose solubility in water.

2. The method according to claim 1, wherein the other vinyl monomer is a member selected from the group consisting of acrylamide, acrylonitrile, methyl acrylate, methyl methacrylate, acrylic acid, methacrylic acid and styrene.

3. The method according to claim 1, wherein the other vinyl monomer is acrylamide.

4. The method according to claim 1, wherein the cationic polymer is applied to soil or water wherein plants are grown or to be grown.

5. The method according to claim 1, wherein the cationic polymer is applied to a surplus sludge produced in an activated sludge treatment, and the resulting dehydrated sludge is applied to soil.

6. The method according to claim 1, wherein the quaternary ammonium compound of the formula (I) is a compound of the formula:

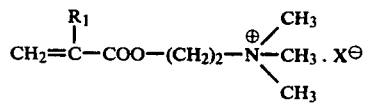

wherein $R_1$ and X are as defined in claim 1.

7. The method of claim 4, wherein the cationic polymers are applied to soil in an amount of up to about 1.0% by weight.

8. The method of claim 7, wherein the cationic polymers are applied in an amount of from 0.01 to 0.5% by weight, based on the weight of the soil.

9. The method of claim 4, wherein the cationic polymers are added to water in an amount of 0.01 to 0.5% by weight, based on the weight of the water.

* * * * *